US010112021B2

(12) United States Patent
Hafner (10) Patent No.: US 10,112,021 B2
(45) Date of Patent: Oct. 30, 2018

(54) INTRANASAL ADMINISTRATION (71) Applicant: OptiNose AS, Oslo (NO)

(72) Inventor: Roderick Peter Hafner, Wiltshire (GB)

(73) Assignee: OptiNose AS, Oslo (NO)

( * ) Notice: Subject to any disclaimer, the term of this patent is extended or adjusted under 35 U.S.C. 154(b) by 0 days.

(21) Appl. No.: 14/635,561

(22) Filed: Mar. 2, 2015

(65) Prior Publication Data

US 2015/0165139 A1 Jun. 18, 2015

Related U.S. Application Data (63) Continuation of application No. 12/303,667, filed as application No. PCT/GB2007/002124 on Jun. 8, 2007.

(30) Foreign Application Priority Data

Jun. 8, 2006 (GB) .................................. 0611312.0

(51) Int. Cl.
*A61M 15/00* (2006.01)
*A61K 9/00* (2006.01)
*A61M 15/08* (2006.01)
*A61K 38/17* (2006.01)
*A61K 38/22* (2006.01)
*A61K 38/28* (2006.01)

(52) U.S. Cl.
CPC ....... *A61M 15/0098* (2014.02); *A61K 9/0043* (2013.01); *A61K 38/1796* (2013.01); *A61K 38/2228* (2013.01); *A61K 38/28* (2013.01); *A61M 15/0091* (2013.01); *A61M 15/08* (2013.01); *A61M 2202/064* (2013.01); *A61M 2210/0618* (2013.01); *A61M 2210/0625* (2013.01)

(58) Field of Classification Search
None
See application file for complete search history.

(56) References Cited

U.S. PATENT DOCUMENTS

| 605,436 | A | 6/1898 | Kellogg |
|---|---|---|---|
| 642,748 | A | 2/1900 | Manners |
| 658,436 | A | 9/1900 | Groth |
| 746,749 | A | 12/1903 | Seidel |
| 902,832 | A | 11/1908 | Philbrook |
| 5,109,120 | A | 4/1992 | Ueno et al. |
| 5,797,392 | A | 8/1998 | Keldmann et al. |
| 6,647,980 | B1 | 11/2003 | Gizurarson |
| 6,648,848 | B1 | 11/2003 | Keldmann et al. |
| 6,715,485 | B1 | 4/2004 | Djupesland |
| D530,815 | S | 10/2006 | Murphy et al. |
| 7,347,201 | B2 | 3/2008 | Djupesland |
| 7,377,901 | B2 | 5/2008 | Djupesland et al. |
| 7,481,218 | B2 | 1/2009 | Djupesland |
| 7,543,581 | B2 | 6/2009 | Djupesland |
| 7,740,014 | B2 | 6/2010 | Djupesland |
| 7,784,460 | B2 | 8/2010 | Djupesland et al. |
| 7,841,337 | B2 | 11/2010 | Djupesland |
| 7,854,227 | B2 | 12/2010 | Djupesland |
| 7,934,503 | B2 | 5/2011 | Djupesland et al. |
| 7,975,690 | B2 | 6/2011 | Djupesland |
| 8,047,202 | B2 | 11/2011 | Djupesland |
| 8,146,589 | B2 | 4/2012 | Djupesland |
| 8,171,929 | B2 | 5/2012 | Djupesland et al. |
| 8,198,240 | B2 | 6/2012 | Yeomans et al. |
| 8,327,844 | B2 | 12/2012 | Djupesland |
| 8,511,303 | B2 | 8/2013 | Djupesland |
| 8,522,778 | B2 | 9/2013 | Djupesland |
| 8,550,073 | B2 | 10/2013 | Djupesland |
| 8,555,877 | B2 | 10/2013 | Djupesland |
| 8,555,878 | B2 | 10/2013 | Djupesland |
| 8,590,530 | B2 | 11/2013 | Djupesland et al. |
| 8,596,278 | B2 | 12/2013 | Djupesland |
| 8,800,555 | B2 | 8/2014 | Djupesland |
| 8,875,704 | B2 | 11/2014 | Djupesland et al. |
| 8,899,229 | B2 | 12/2014 | Djupesland et al. |
| 8,910,629 | B2 | 12/2014 | Djupesland et al. |
| D723,156 | S | 2/2015 | Djupesland et al. |
| D725,769 | S | 3/2015 | Djupesland et al. |
| 8,978,647 | B2 | 3/2015 | Djupesland et al. |
| 9,010,325 | B2 | 4/2015 | Djupesland et al. |
| 9,038,630 | B2 | 5/2015 | Djupesland et al. |
| 9,067,034 | B2 | 6/2015 | Djupesland et al. |
| 9,072,857 | B2 | 7/2015 | Djupesland |

(Continued)

FOREIGN PATENT DOCUMENTS

| WO | WO 96/22802 | 8/1996 |
|---|---|---|
| WO | WO 98/53869 | 12/1998 |

(Continued)

OTHER PUBLICATIONS

Guy Furness. Nasal drug delivery: rapid onset via a convenient route. ONdrugDelivery Ltd. 2005. Registered in England: No. 05314696.*
Dankesreiter et al. Synthetic Endotoxin-Binding Peptides Block Endotoxin-Triggered TNF-Production by Macrophages in Vitro and in Vivo and Prevent Endotoxin-Mediated Toxic Shock. The Journal of Immunology, 2000, 164: 4804-4811. (Year: 2000).*
L. Illum, *Nasal drug delivery—possibilities, problems and solutions*, J Control Release (Feb. 21, 2003).
Cindy H. Dubin, *Nothing to Sneeze At*, Pharmaceutical Formulation & Quality Magazine (Jan. 29, 2003).
Per Gisle Djupesland, *Nasal Delivery of Vaccines*, EPC (Jan. 29, 2003).

(Continued)

*Primary Examiner* — Marcela M Cordero Garcia
*Assistant Examiner* — Jia-Hai Lee
(74) *Attorney, Agent, or Firm* — Finnegan, Henderson, Farabow, Garrett & Dunner LLP (57) ABSTRACT

Intranasal administration of proteins, such as insulin and insulin analogues, in particular immunogenic proteins to the upper posterior region of a nasal cavity of a subject, and in particular the olfactory bulb region.

34 Claims, 4 Drawing Sheets

(56) References Cited

U.S. PATENT DOCUMENTS

| | | |
|---|---|---|
| 9,108,015 B2 | 8/2015 | Djupesland |
| 9,119,932 B2 | 9/2015 | Djupesland |
| 9,132,249 B2 | 9/2015 | Djupesland |
| 9,144,652 B2 | 9/2015 | Djupesland et al. |
| 9,168,341 B2 | 10/2015 | Djupesland |
| 9,205,208 B2 | 12/2015 | Djupesland |
| 9,205,209 B2 | 12/2015 | Djupesland |
| 9,272,104 B2 | 3/2016 | Djupesland |
| D759,805 S | 6/2016 | Djupesland |
| D761,951 S | 7/2016 | Djupesland |
| 9,452,272 B2 | 9/2016 | Djupesland et al. |
| 9,468,727 B2 | 10/2016 | Djupesland |
| 2004/0024330 A1 | 2/2004 | Djupesland et al. |
| 2004/0112378 A1 | 6/2004 | Djupesland |
| 2004/0112379 A1 | 6/2004 | Djupesland |
| 2004/0112380 A1 | 6/2004 | Djupesland |
| 2004/0149289 A1 | 8/2004 | Djupesland |
| 2004/0182388 A1 | 9/2004 | Djupesland |
| 2005/0028812 A1 | 2/2005 | Djupesland |
| 2005/0072430 A1 | 4/2005 | Djupesland |
| 2005/0235992 A1 | 10/2005 | Djupesland |
| 2006/0096589 A1 | 5/2006 | Djupesland |
| 2006/0107957 A1 | 5/2006 | Djupesland |
| 2006/0169278 A1 | 8/2006 | Djupesland et al. |
| 2006/0219240 A1 | 10/2006 | Djupesland |
| 2006/0219241 A1 | 10/2006 | Djupesland |
| 2006/0225732 A1 | 10/2006 | Djupesland |
| 2006/0231094 A1 | 10/2006 | Djupesland |
| 2007/0039614 A1 | 2/2007 | Djupesland |
| 2007/0125371 A1 | 6/2007 | Djupesland |
| 2007/0186927 A1 | 8/2007 | Djupesland et al. |
| 2008/0161771 A1 | 7/2008 | Djupesland |
| 2008/0163874 A1 | 7/2008 | Djupesland |
| 2008/0221471 A1 | 9/2008 | Djupesland et al. |
| 2008/0223363 A1 | 9/2008 | Djupesland |
| 2008/0289629 A1 | 11/2008 | Djupesland et al. |
| 2009/0101146 A1 | 4/2009 | Djupesland |
| 2009/0181880 A1 | 7/2009 | Yeomans et al. |
| 2009/0293873 A1 | 12/2009 | Djupesland et al. |
| 2009/0304802 A1 | 12/2009 | Djupesland et al. |
| 2009/0314293 A1 | 12/2009 | Djupesland |
| 2009/0320832 A1 | 12/2009 | Djupesland |
| 2010/0035805 A1 | 2/2010 | Hafner |
| 2010/0051022 A1 | 3/2010 | Djupesland et al. |
| 2010/0057047 A1 | 3/2010 | Djupesland et al. |
| 2010/0242959 A1 | 9/2010 | Djupesland et al. |
| 2010/0282246 A1 | 11/2010 | Djupesland et al. |
| 2010/0288275 A1 | 11/2010 | Djupesland et al. |
| 2010/0300439 A1 | 12/2010 | Djupesland et al. |
| 2011/0023869 A1 | 2/2011 | Djupesland |
| 2011/0053827 A1 | 3/2011 | Hafner |
| 2011/0088690 A1 | 4/2011 | Djupesland et al. |
| 2011/0088691 A1 | 4/2011 | Djupesland |
| 2011/0114087 A1 | 5/2011 | Djupesland |
| 2011/0126830 A1 | 6/2011 | Djupesland et al. |
| 2011/0259329 A1 | 10/2011 | Djupesland et al. |
| 2011/0318345 A1 | 12/2011 | Djupesland |
| 2012/0000459 A1 | 1/2012 | Djupesland |
| 2012/0006323 A1 | 1/2012 | Djupesland |
| 2012/0073571 A1 | 3/2012 | Djupesland |
| 2012/0090608 A1 | 4/2012 | Djupesland et al. |
| 2012/0260915 A1 | 10/2012 | Djupesland |
| 2013/0098362 A1 | 4/2013 | Djupesland et al. |
| 2013/0125889 A1 | 5/2013 | Djupesland et al. |
| 2013/0327320 A1 | 12/2013 | Djupesland |
| 2014/0018295 A1 | 1/2014 | Djupesland |
| 2014/0041660 A1 | 2/2014 | Djupesland et al. |
| 2014/0060536 A1 | 3/2014 | Djupesland |
| 2014/0073562 A1 | 3/2014 | Djupesland |
| 2014/0144442 A1 | 5/2014 | Djupesland et al. |
| 2014/0144443 A1 | 5/2014 | Djupesland et al. |
| 2014/0166008 A1 | 6/2014 | Djupesland |
| 2014/0202456 A1 | 7/2014 | Djupesland |
| 2014/0246022 A1 | 9/2014 | Djupesland et al. |
| 2015/0007811 A1 | 1/2015 | Djupesland et al. |
| 2015/0013670 A1 | 1/2015 | Djupesland et al. |
| 2015/0013677 A1 | 1/2015 | Djupesland et al. |
| 2015/0053201 A1 | 2/2015 | Djupesland et al. |
| 2015/0090259 A1 | 4/2015 | Djupesland et al. |
| 2015/0101605 A1 | 4/2015 | Djupesland et al. |
| 2015/0144129 A1 | 5/2015 | Djupesland et al. |
| 2015/0165139 A1 | 6/2015 | Hafner |
| 2015/0182709 A1 | 7/2015 | Djupesland |
| 2015/0246194 A1 | 9/2015 | Djupesland et al. |
| 2015/0367090 A1 | 12/2015 | Djupesland et al. |
| 2015/0367091 A1 | 12/2015 | Djupesland et al. |
| 2016/0001022 A1 | 1/2016 | Djupesland et al. |
| 2016/0045687 A1 | 2/2016 | Djupesland |
| 2016/0051778 A1 | 2/2016 | Djupesland et al. |
| 2016/0074603 A1 | 3/2016 | Djupesland et al. |
| 2016/0082206 A1 | 3/2016 | Djupesland et al. |
| 2016/0082207 A1 | 3/2016 | Djupesland et al. |
| 2016/0166788 A1 | 6/2016 | Djupesland et al. |
| 2016/0184537 A1 | 6/2016 | Djupesland |
| 2016/0193435 A1 | 7/2016 | Djupesland |
| 2016/0250408 A1 | 9/2016 | Djupesland |
| 2016/0263334 A1 | 9/2016 | Djupesland |
| 2016/0279357 A1 | 9/2016 | Djupesland |
| 2016/0310683 A1 | 10/2016 | Djupesland et al. |

FOREIGN PATENT DOCUMENTS

| | | | |
|---|---|---|---|
| WO | WO 00/51672 | 9/2000 | |
| WO | WO 01/97689 | 12/2001 | |
| WO | WO 2002/000282 | 1/2002 | |
| WO | WO 02/068029 | 9/2002 | |
| WO | WO 02/068030 | 9/2002 | |
| WO | WO 02/068031 | 9/2002 | |
| WO | WO 02/068032 | 9/2002 | |
| WO | WO 03/000310 | 1/2003 | |
| WO | WO 03/020350 | 3/2003 | |
| WO | WO 03/082393 | 10/2003 | |
| WO | WO 03/084591 | 10/2003 | |
| WO | WO 03/090812 | 11/2003 | |
| WO | WO 2004/004814 | 1/2004 | |
| WO | WO 2004/004922 | 1/2004 | |
| WO | WO 2004/060433 | 7/2004 | |
| WO | WO 2004/103447 | 12/2004 | |
| WO | WO 2005/004838 | 1/2005 | |
| WO | WO 2005/016423 | 2/2005 | |
| WO | WO 2005/021059 | 3/2005 | |
| WO | WO 2006/030210 | 3/2006 | |
| WO | WO2006030210 A2 * | 3/2006 | ............ A61M 15/00 |
| WO | WO 2006/090149 | 8/2006 | |
| WO | WO 2007/083073 | 7/2007 | |
| WO | WO 2007/093784 | 8/2007 | |
| WO | WO 2007/093791 | 8/2007 | |
| WO | WO 2007/099361 | 9/2007 | |
| WO | WO 2007/102089 | 9/2007 | |
| WO | WO 2007/107887 | 9/2007 | |
| WO | WO 2007/125318 | 11/2007 | |
| WO | WO 2007/141541 | 12/2007 | |
| WO | WO 2008/012531 | 1/2008 | |
| WO | WO 2008/042452 | 4/2008 | |
| WO | WO 2008/065403 | 6/2008 | |
| WO | WO 2008/081326 | 7/2008 | |
| WO | WO 2008/081327 | 7/2008 | |
| WO | WO 2008/122791 | 10/2008 | |
| WO | WO 2008/122795 | 10/2008 | |
| WO | WO 2009/044172 | 4/2009 | |
| WO | WO 2010/029441 | 3/2010 | |
| WO | WO 2012/035427 | 3/2012 | |
| WO | WO 2012/123819 | 9/2012 | |
| WO | WO 2013/124491 | 8/2013 | |
| WO | WO 2013/124492 | 8/2013 | |
| WO | WO 2013/124493 | 8/2013 | |
| WO | WO 2014/155192 | 10/2014 | |

OTHER PUBLICATIONS

Per Gisle Djupesland, *Who Nose How Far Nasal Delivery Can Go?*, EPC (Oct. 7, 2003).

Per Gisle Djupesland, *Bi-directional Nasal Drug Delivery*, Innovations in Pharmaceutical Technology (Jul. 10, 2004).

(56) References Cited

OTHER PUBLICATIONS

P.G. Djupesland, *Bi-Directional Nasal Delivery of Aerosols Can Prevent Lung Deposition*, Journal of Aerosol Medicine (Sep. 2004).
*Bi-Directional Nasal Device Delivers Drug on Exhalation*, Pharmaceutical Technology (Sep. 10, 2004).
Ola Dale et al., *Intranasal Midazolam: A Comparison of Two Delivery Devices in Human Volunteers*, Journal of Pharmacy and Pharmacology (Oct. 2004).
M. Kleven, *Using Computational Fluid Dynamics (CFD) to Improve the Bi-Directional Nasal Drug Delivery Concept*, Trans IChemE Part C. (Jun. 2005).
Per Gisle Djupesland, *Breath-Actuated Bi-Directional Delivery Sets the Nasal Market on a New Course*, ONdrugDelivery (Oct. 10, 2005).
Hilde Bakke et al., *Oral Spray Immunization May be an Alternative to Intranasal Vaccine Delivery to Induce Systemic Antibodies But Not Nasal Mucosal or Cellular Immunity*, Scan J. of Immunol. (Mar. 2006).
P.G. Djupesland et al., *Breath Actuated Nasal Device Improves Delivery to Target Sites Beyond the Nasal Valve*, The Laryngoscope (Mar. 2006).
R. Luthringer et al., *Rapid Absorption of Sumatriptan Powder and Effects on Glyceryl tinitrate Model of Headache Following Intranasal Delivery Using a Novel Bi-Directional Device*, Journal of Pharmacy and Pharmacology (Jan. 2009).
A. Skretting et al., *A New Method for Scintigraphic Quantification of Deposition and Clearance in Anatomical Regions of the Human Nose*, Nuclear Medicine Communications (Aug. 2009).
Vlckovia et al., *Effective Treatment of Mild-to-Moderate Nasal Polyposis with Fluticasone Delivered by a Novel Device*, Rhinology (Oct. 22, 2009).
Per Gisle Djupesland et al., *Impact of Baseline Nasal Polyp Size and Previous Surgery on Efficacy of Fluticasone Delivered With a Novel Device: A Subgroup Analysis*, Am. J. Rhinology Allergy (2010).
P.G. Djupesland et al., *Intranasal Sumatriptan Powder Delivered by a Novel Breath Actuated Bi-Directional Device for the Acute Treatment of Migraine: A Randomised Placebo-Controlled Study*, Cephalalgia (Mar. 17, 2010).
F.S. Hansen et al., *Preliminary Efficacy of Fluticasone Delivered by a Novel Device in Recalcitrant Chronic Rhinosinusitis*, Rhinology (Jun. 26, 2010).
Per Gisle Djupesland, *Nasal Drug Delivery Devices: Characteristics and Performance in Clinical Perspective—A Review*, Drug. Deliv. and Transl. Res. (Oct. 18, 2012).
Per Gisle Djupesland, *Nasal Deposition and Clearance in Man: Comparison of a Bidirectional Powder Device and a Traditional Liquid Spray Pump*, Journal of Aerosol Medicine and Pulmonary Drug Delivery (Nov. 2012).
Stewart J. Tepper, *Clinical Implications for Breath-Powered Powder Sumatriptan Intranasal Treatment*, Headache, The American Headache Society (Apr. 29, 2013).
Mohammad Obaidi et al., *Improved Pharmacokinetics of Sumatriptan With Breath Powered Nasal Delivery of Sumatriptan Powder*, Headache, The American Headache Society (May 24, 2013).
Per Gisle Djupesland, *Breath Powdered Nasal Delivery: A New Route to Rapid Headache Relief*, Headache, The American Headache Society (Jun. 4, 2013).
Per Gisle Djupesland et al., *The Nasal Approach to Delivering Treatment for Brain Diseases: An Anatomic, Physiologic, and Delivery Technology Overview*, Therapeutic Delivery (2014).
R.K. Cady et al., *A Randomized Double-Blind, Placebo Controlled Study of Breath Powered Nasal Delivery of Sumatriptan Powder (AVP-825) in the Treatment of Acute Migraine (The TARGET Study)*, Headache (Sep. 8, 2014).
S.J. Tepper et al., *AVP-825 Breath-Powdered Intranasal Delivery System Containing 22 mg Sumatriptan Powder vs. 100 mg Oral Sumatripta in the Acute Treatment of Migraines (The COMPASS Study): A Comparative Randomized Clinical Trial Across Multiple Attacks*, Headache: The Journal of Head and Face Pain (Mar. 29, 2015).
D. S. Quintana et al., *Low-dose Oxytocin Delivered Intranasally with Breath Powdered Device Affects Social-Cognitive Behavior: A Randomized Four-Way Crossover Trial with Nasal Cavity Dimension Assessment*, Transl Psychiatry (Jul. 14, 2015).
R. Mahmoud, *Breathe Out*, Innovations in Phar, Tech. (Dec. 10, 2015).
Fine et al., "Autism spectrum disorders and symptoms in children with molecularly confirmed 22q11.2 deletion syndrome," J Autism Dev Disord, 35(4):461-470, (2005).
Caradang et al., "Metyrosine in psychosis associated with 22q11.2 deletion syndrome: case report," J Child Adolesc Psychopharmacol, 17(1):115-120, (2007).
Guastella et al., "Intranasal oxytocin improves emotion recognition for youth with autism spectrum disorders," Biol Psychiatry, 67(7):692-694, (2010).
Ross et al., "Oxytocin and the neural mechanisms regulating social cognition and affiliative behavior," Front Neuroendocrinol, 30(4):534-547, (2009).

* cited by examiner

INTRANASAL ADMINISTRATION

CROSS REFERENCE TO RELATED APPLICATIONS

This application is a continuation of U.S. application Ser. No. 12/303,667, filed Nov. 1, 2010, which is a US national phase application of PCT/GB07/02124, filed Jun. 8, 2007, which claims priority to GB 0611312.0, filed on Jun. 8, 2006, all of which applications are incorporated herein by reference.

FIELD OF INVENTION

The present invention relates to intranasal administration of proteins, such as insulin and insulin analogues, in particular immunogenic proteins to the upper posterior region of a nasal cavity of a subject, and in particular the olfactory bulb region.

BACKGROUND

Recent studies have demonstrated that the intranasal administration of insulin acts to improve memory and has an effect on obesity [1-8].

However, other studies have shown that intranasal administration of insulin over an extended period, typically six months, results in antibodies being raised to insulin [9].

Whilst the authors of this publication argue that the raising of antibodies to insulin could be beneficial in terms of being protective of loss of beta cell function in individuals at risk of Type I diabetes, there is no recognition that raising a neutralising antibody response to insulin would be of particular concern in patients with obesity who may be at risk of developing Type II diabetes and where there is limited additional capacity for the pancreas further to increase insulin production. It would also be inappropriate to increase neutralising antibody levels to insulin in patients who already have insulin loss as this may worsen the condition.

It is an aim of the present invention to provide for the intranasal administration of proteins, such as insulin and insulin analogues, and in particular by the applicant's bi-directional methodology, as disclosed in the applicant's earlier WO-A-2000/051672, the content of which is incorporated herein by reference.

Delivery of vaccine antigens by the bi-directional methodology has been shown to date to provide an increase in the circulating antibodies when compared to intranasal administration by conventional nasal spray technologies, in particular nasal spray pumps. As such, a person skilled in the art would have contemplated that intranasal administration of insulin using bi-directional delivery technology should increase the immune response to insulin and other immunogenic proteins, which is contrary to the requirement for delivery of proteins and peptides to the CNS.

Figure 1:
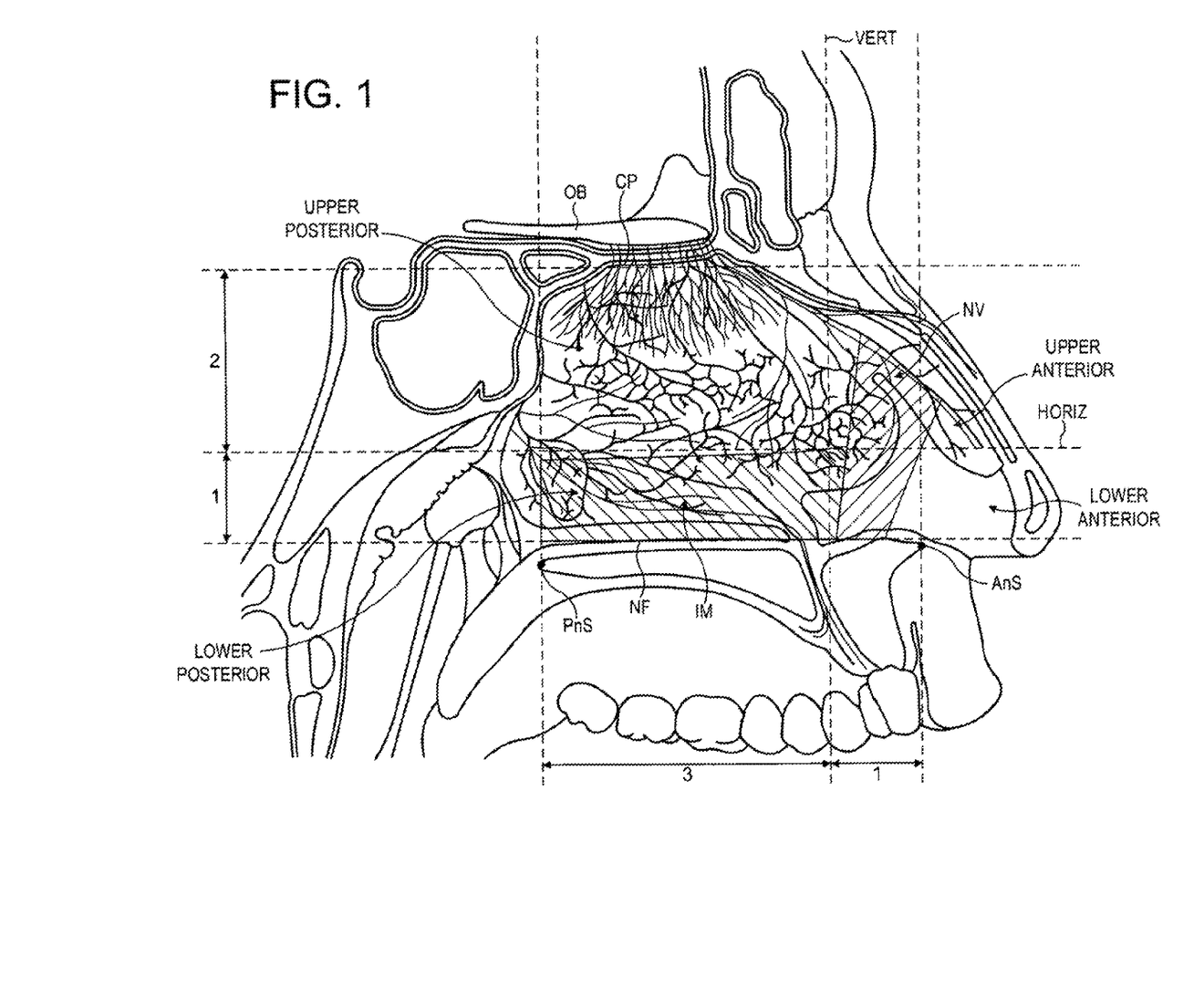
FIG. 1 illustrates the segmentation of a nasal cavity in accordance with a preferred embodiment of the present invention.

It is a particular aim of the present invention to provide for the intranasal administration of proteins, such as insulin and insulin analogues, in therapeutically-significant amounts to the olfactory bulb region in the upper posterior region of the nasal cavity, such that the proteins access the CNS and avoid being presented to the nasal associated lymphatic tissue (NALT) which includes M-cells, as encompassed by Waldeyer's ring, and in particular in the adenoids, and antigen presenting cells (APCs) which are widely distributed throughout the nasal mucosa, which would cause a neutralising antibody response. The posterior region of the nasal airway is that region which is posterior of the nasal valve NV, as illustrated in FIG. 1. The nasal valve comprises the anterior bony cavum which contains inferior turbinate erectile tissue and septal erectile tissue, which are supported respectively by compliant ala tissue and the rigid cartilaginous septum [10]. These elements combine to form a dynamic valve, which extends over several millimetres, that adjusts nasal airflow, and is stabilized by cartilage and bone, modulated by voluntary muscle and regulated by erectile tissue. The lumen of the nasal valve is the section of narrowest cross-sectional area between the posterior and anterior regions of the nasal airway, and is much longer and narrower dorsally than ventrally, and this lumen defines a triangular entrance which extends to the piriform region of the bony cavum. The nasal valve is lined in its anterior part with transitional epithelium, with a gradual transition posterior to respiratory epithelium. The nasal valve and anterior vestibule define roughly the anterior one-third of the nose.

The posterior region of the nasal airway is that region which is lined with respiratory epithelium, which is ciliated, and olfactory epithelium, which comprises nerves which extend downwards through the cribiform plate CP from the olfactory bulb OB and defines the olfactory bulb region, whereas the anterior region of the nasal airway is that region which is lined with squamous epithelium, which is not ciliated, and transitional epithelium. The olfactory epithelium extends on both the lateral and medial sides of the nasal airway which defines the olfactory cleft, and typically extends downwards about 1.5 to 2.5 cm.

The upper posterior region is the region above the inferior meatus IM, as illustrated in FIG. 1, and encompasses the middle turbinate, the middle meatus, the sinus ostia in infundibulum (ostia to maxillary, frontal and ethmoidal sinuses), the olfactory region, and the upper branches of the trigeminal nerve, and is that region which includes veins which drain to the venous sinuses that surround the brain.

As illustrated in FIG. 1, the posterior region of the nasal airway is the nasal region posterior of an imaginary vertical plane VERT which is located at a position corresponding to the lower angle of the anterior nasal aperture (aperture piriformis), which corresponds substantially to one-quarter of the distance between the anterior nasal spine AnS, which is a pointed projection at the anterior extremity of the intermaxillary suture, and the posterior nasal spine PnS, which is the sharp posterior extremity of the nasal crest of the hard palate and represents the transition between the nose and the nasopharynx, which corresponds to a distance posterior of the anterior nasal spine AnS of between about 13 mm and about 14 mm (Rosenberger [11] defines the distance between the anterior nasal spine AnS and the posterior nasal spine PnS as being 56 mm in eighteen year old boys and 53.3 mm in eighteen year old girls).

As further illustrated in FIG. 1, the upper region of the nasal airway is an upper segment of the nasal airway which is bounded by the cribiform plate CP and a horizontal plane HORIZ which is located at a position corresponding to one-third of the distance between the nasal floor NF of the nasal airway and the cribiform plate CP, which corresponds to a height of typically between about 13 and about 19 mm above the nasal floor NF (Zacharek et al [12] define the distance from the nasal floor NF to the cribiform plate CP as 46+/−4 mm).

The upper posterior region is thus that upper posterior region which is bounded by the above-defined vertical and horizontal planes VERT, HORIZ.

It is a further aim of the present invention to provide for the intranasal administration of proteins, such as insulin and insulin analogues, such that the proteins which are not absorbed into the CNS remain in solution and are not phagocytosed by immunogenic cells, such as the antigen presenting cells.

It is a still further aim of the present invention to provide for the intranasal administration of proteins, such as insulin and insulin analogues, and in particular where delivered as a powdered formulation, such that a minimal amount of associated endotoxin is delivered therewith, so as to avoid triggering the maturation of immature antigen presenting cells.

It is a yet further aim of the present invention to provide that the intranasal administration of insulin, in particular in the treatment of Alzheimer's disease and obesity, does not result in the exacerbation or precipitation of type II diabetes.

BRIEF SUMMARY OF THE INVENTION

In one aspect the present invention provides for selective delivery of immunogenic proteins to the upper posterior region of the nasal cavity, and in particular the olfactory bulb region, such as to provide for uptake of an immunogenic protein to the CNS without triggering a significant immune response.

In another aspect the present invention provides for an administration methodology which minimizes the delivery of endotoxins.

In one embodiment the nosepiece of the delivery device is configured to prevent the accumulation of endotoxins thereon, such as by way of an agent, for example, as a coating, which degrades polysaccharides, which represent the immunogenic component of endotoxins, for example, by way of binding to the polysaccharide. In one embodiment a cap for the nosepiece could similarly include such an agent.

In another embodiment the nosepiece of the delivery device is replaceable. With this methodology, the accumulation of endotoxins on the nosepiece, as would occur through repeated use, is prevented.

In another aspect the present invention provides a solubilized protein formulation which is formulated, such as by including one or more solubilizing agents, to provide for the protein to remain in solution following intranasal administration.

In this way, the one or more proteins do not precipitate out of solution following administration, for example, owing to a shift in pH, ionic balance or osmolarity, which would result in undesirable phagocytosation of the protein by the antigen presenting cells.

In a further aspect the present invention provides for a powdered protein formulation which provides for the rapid and complete dissolution of the protein following administration.

Powdered protein formulations may have advantages in terms of stability, but are likely to result in insoluble particles being phagocytosed by the antigen presenting cells. The present inventors have recognized that this can be overcome by ensuring that the powder particles are rapidly hydrated following administration.

In a still further aspect the present invention provides for a protein formulation which includes an immunomodulator, which acts to prevent an immune response to the administered protein.

In a yet still further aspect the present invention provides for a protein formulation which is formulated to degrade any of the protein which remains to be absorbed within 15 minutes, and preferably 10 minutes, following administration.

With this formulation, any of the protein which is transported by the mucociliary clearance mechanisms to the nasal associated lymphatic tissue and the antigen presenting cells is degraded such that no immune response is raised to the protein.

In yet another aspect the present invention provides a protein formulation which is formulated to ensure uptake from the olfactory bulb region within 10 minutes following administration.

In one embodiment the formulation includes an uptake agent, such as a cyclodextrin, for providing for rapid uptake of the protein in the olfactory bulb region.

In another embodiment, where the formulation is delivered by the bi-directional methodology, the particle sizes of the delivered formulation and the flow rate of the entraining gas flow are such as to provide for targeted delivery to and efficient transfer across the olfactory bulb region, such as to provide for a much reduced antibody response as compared to delivery by conventional nasal spray technology, in particular nasal spray pumps.

With this formulation, none of the protein remains to be transported by the mucociliary clearance mechanisms to the nasal associated lymphatic tissue, including the specialized M-cells, and the antigen presenting cells.

In yet another aspect the present invention provides a delivery device for delivering a substance to the nasal airway of a subject, the delivery device including a nosepiece having a replaceable outer sleeve, with the sleeve preferably including an indicator material which provides an indication of exposure to one or more of moisture and biomaterials, such as endotoxins.

In yet still another aspect the present invention provides a delivery device for delivering a substance to the nasal airway of a subject, the delivery device including a nosepiece having a plurality of removable sleeves which are removable successively to allow for exposure of a fresh sleeve, with the sleeves preferably including an indicator material which provides an indication of exposure to one or more of moisture and biomaterials, such as endotoxins.

BRIEF DESCRIPTION OF THE DRAWINGS

Preferred embodiments of the present invention will now be described hereinbelow by way of example only with reference to the accompanying drawings, in which.

DETAILED DESCRIPTION OF THE INVENTION

Figure 2:
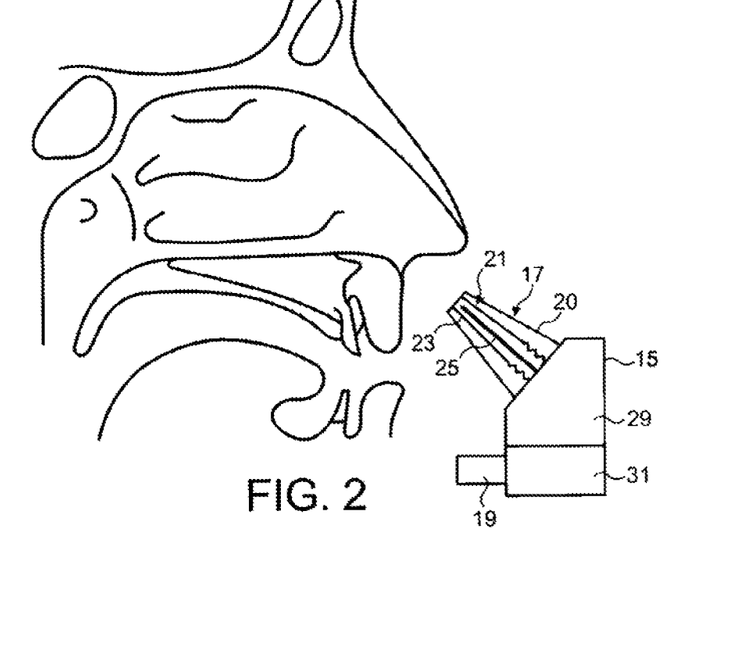
FIG. 2 schematically illustrates a nasal delivery device for delivering a protein formulation to a nasal airway of a subject in accordance with one embodiment of the present invention.

The delivery device comprises a housing 15, a nosepiece unit 17 for fitting in a nasal cavity of a subject, and a mouthpiece 19 through which the subject exhales to actuate the delivery device.

Figure 3:
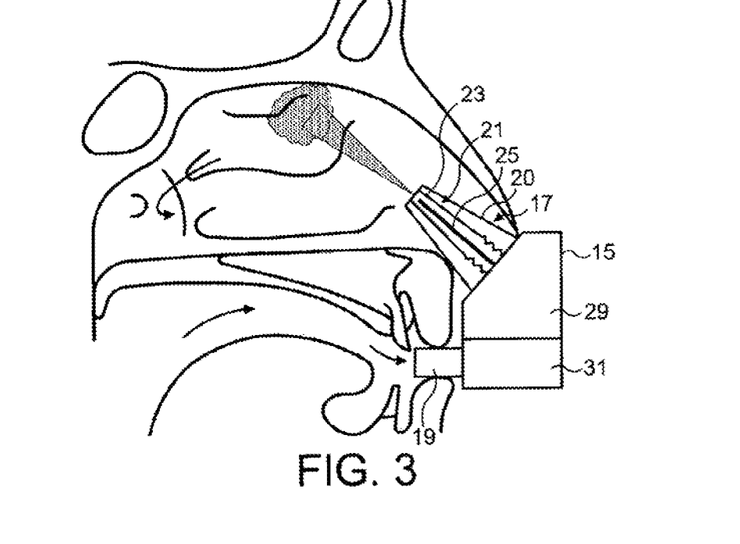
FIG. 3 illustrates the delivery device of FIG. 2 where operative to deliver a dose of the embodied protein formulation into the nasal airway of the subject.

The nosepiece unit 17 comprises a nosepiece 20, in this embodiment a frusto-conical element, for guiding the nosepiece unit 17 into a nasal passage of the subject and being configured both to provide a fluid-tight seal with the naresi of the nostril and obstruct, in this embodiment close, the nasal passage at a position therealong, in this embodiment at a position corresponding substantially to the nasal valve, thereby obstructing the anterior one-third of the nasal passage and leaving open the posterior two-thirds of the nasal passage, as illustrated in FIG. 3, and an outlet unit 21 for delivering substance, in this embodiment a protein formulation containing insulin, to an upper posterior region of the nasal passage of the subject, in this embodiment an upper posterior region as bounded by a vertical plane which is located posterior of the anterior nasal spine AnS at a position corresponding to one-quarter of the distance between the anterior and posterior nasal spines AnS, PnS and a horizontal plane which is located above the nasal floor at a height one-third of the distance between the nasal floor and the cribiform plate, which encompasses the olfactory bulb region from which the substance is uptaken into the CNS of the subject.

In this embodiment the delivery device is re-usable, and the nosepiece 20 is replaceable, such as to prevent the accumulation of endotoxins thereon, which could be transferred to the nasal cavity of the subject.

In an alternative embodiment the nosepiece 20 could be configured to prevent accumulation of endotoxins thereon, such as by including an anti-bacterial.

In this embodiment the outlet unit 21 comprises a delivery channel 23 which is in fluid communication with the mouthpiece 19 such that an air flow is delivered into and through the nasal airway of the subject on exhalation by the subject through the mouthpiece 19, and a nozzle 25 for delivering the nasal formulation to the nasal airway of the subject.

In this embodiment the nozzle 25 is configured to deliver an aerosol spray, either as a liquid or a powder aerosol spray, but in an alternative embodiment the nozzle could be configured to deliver a jet, that is, as a column of the formulation, either as a liquid or powder jet.

The delivery device further comprises a substance supply unit 29 for delivering metered doses of the formulation, which is fluidly connected to the nozzle 25 to deliver the nasal formulation from the nosepiece 17, in this embodiment as an aerosol spray.

In this embodiment the substance supply unit 29 comprises a mechanical delivery pump, in particular a liquid delivery pump or a powder delivery pump, which delivers metered doses of substance, on actuation thereof.

In another alternative embodiment the substance supply unit 29 could comprise a dry powder delivery unit which delivers metered doses of substance, as a dry powder, on actuation thereof. In one embodiment the substance supply unit 29 could provide for delivery of substance from a capsule.

In yet another alternative embodiment the substance supply unit 29 could comprise an aerosol canister which delivers metered volumes of a propellant, preferably a hydrofluoroalkane (HFA) propellant or the like, containing substance, either as a suspension or solution.

In this embodiment the substance supply unit 29 is a multi-dose unit for delivering a plurality of metered doses of the nasal formulation. In another embodiment the substance supply unit 29 could be a single-dose unit for delivering a single metered dose of the nasal formulation.

The substance supply unit 29 is pre-primeable, in this embodiment by loading a resilient element, and includes a breath-actuated release mechanism 31 which, when triggered, releases the resilient element and actuates the substance supply unit 29 to deliver a metered dose of the nasal formulation through the nozzle 25.

In this embodiment the trigger mechanism 31 is configured to cause actuation of the substance supply unit 29 on generation of a predetermined flow rate through the delivery channel 23.

In one embodiment the protein formulation comprises a solubilized protein formulation.

In one embodiment the solution comprises a viscous solution, such as a gel.

In one embodiment the protein formulation is such as to remain in solution following delivery, and preferably includes a solubilizing agent for maintaining the protein in solution following delivery.

In one embodiment the protein formulation is such that the protein does not precipitate from solution owing to one or more of a shift in pH, ionic balance or osmolarity following delivery.

In an alternative embodiment the protein formulation could be a powdered protein formulation.

In one embodiment the powdered protein formulation provides for dissolution of the protein following delivery.

Preferably, the powdered protein formulation provides for dissolution of the protein within about 5 minutes of delivery.

More preferably, the powdered protein formulation provides for dissolution of the protein within about 2 minutes of delivery.

Still more preferably, the protein formulation provides for dissolution of the protein within about 1 minute of delivery.

In one embodiment the protein formulation includes an immunomodulator, which acts to prevent an immune response to the protein.

In one embodiment the protein formulation is such as to degrade the protein which remains to be absorbed subsequent to a predeterminable period following delivery.

In one embodiment the protein formulation includes a proteolytic agent which acts to degrade the protein which remains to be absorbed subsequent to the predeterminable period following delivery.

In one embodiment the proteolytic agent can include one or more of trypsin, chymotrypsin, N terminal peptidases and C terminal peptidases.

Preferably, the protein formulation is such as to degrade the protein which remains to be absorbed within about 15 minutes following delivery.

More preferably, the protein formulation is such as to degrade the protein which remains to be absorbed within about 10 minutes following delivery.

Still more preferably, the protein formulation is such as to degrade the protein which remains to be absorbed within about 5 minutes following delivery.

In one embodiment the protein formulation provides for rapid uptake of the protein from the olfactory bulb region in the upper posterior region.

In one embodiment the protein formulation includes an uptake agent for providing for uptake of the protein from the olfactory bulb region.

In one embodiment the uptake agent is a cyclodextrin.

Preferably, the protein formulation provides for uptake of the protein from the olfactory bulb region within about 10 minutes following delivery.

More preferably, the protein formulation provides for uptake from the olfactory bulb region within about 5 minutes following delivery.

In an alternative embodiment the protein formulation comprises an antidiuretic hormone, such as argipressin, lypressin, desmopressin, felypressin, ornipressin, terlipressin and vasopressin or their pharmaceutically-acceptable derivatives or analogues.

In an alternative embodiment the protein formulation comprises an oxytocic hormone, such as carbetocin, demoxytocin and oxytocin or their pharmaceutically-acceptable derivatives or analogues.

In an alternative embodiment the protein formulation comprises an oxytocin antagonist, such as atosiban or its pharmaceutically-acceptable derivatives or analogues.

In an alternative embodiment the protein formulation comprises a corticotrophic hormone, such as corticotrophin and tetracosactide or their pharmaceutically-acceptable derivatives or analogues.

In an alternative embodiment the protein formulation comprises a corticotrophic releasing hormone, such as corticorelin or its pharmaceutically-acceptable derivatives or analogues.

In an alternative embodiment the protein formulation comprises an omatotrophic hormone, such as mecasermin, somatrem and somatropin or their pharmaceutically-acceptable derivatives or analogues.

In an alternative embodiment the protein formulation comprises a somatotrophic hormone receptor antagonist, such as pegvisomant or its pharmaceutically-acceptable derivatives or analogues.

In an alternative embodiment the protein formulation comprises an omatotrophic releasing hormone, such as sermorelin and somatorelin or their pharmaceutically-acceptable derivatives or analogues.

In an alternative embodiment the protein formulation comprises a somatotrophic release inhibitor, such as lanreotide, octreotide, somatostatin and vapreotide or their pharmaceutically-acceptable derivatives or analogues.

In an alternative embodiment the protein formulation comprises a gonadotrophic hormone, such as choriogonadotrophin alfa, chorionic gonadotrophin, a follicle stimulating hormone, follitropin alfa, follitropin beta, a luteinising hormone, lutropin alfa, menotrophin and urofollitropin or their pharmaceutically-acceptable derivatives or analogues.

In an alternative embodiment the protein formulation comprises a gonadotrophic releasing hormone, such as buserelin, deslorelin, gonadorelin, goserelin, histrelin, leuprorelin, naferlin and triptorelin or their pharmaceutically-acceptable derivatives or analogues.

In an alternative embodiment the protein formulation comprises an onadotrophic releasing hormone antagonist, such as abarelix, cetorelix and ganirelix or their pharmaceutically-acceptable derivatives or analogues.

In an alternative embodiment the protein formulation comprises a thyrotrophic hormone, such as thyrotrophin and thyrotrophin alfa or their pharmaceutically-acceptable derivatives or analogues.

In an alternative embodiment the protein formulation comprises a thyrotrophic releasing hormone, such as posatirelin, protirelin and taltirelin or their pharmaceutically-acceptable derivatives or analogues.

In an alternative embodiment the protein formulation comprises a lactotrophic hormone, such as prolactin or its pharmaceutically-acceptable derivatives or analogues.

In an alternative embodiment the protein formulation comprises a metabolic peptide, such as an insulin-like growth factor, a glucagon, a growth hormone and PYY3-36 or their pharmaceutically-acceptable derivatives or analogues.

In an alternative embodiment the protein formulation comprises calcitonin or pharmaceutically-acceptable derivatives or analogues thereof, such as elcatonin and salcatonin.

In an alternative embodiment the protein formulation comprises a melanocyte stimulating hormone.

In an alternative embodiment the protein formulation comprises a nerve growth factor.

In an alternative embodiment the protein formulation comprises an epidermal growth factor.

In an alternative embodiment the protein formulation comprises an epoetin or its pharmaceutically-acceptable derivatives or analogues.

In an alternative embodiment the protein formulation comprises an interleukin.

In an alternative embodiment the protein formulation comprises a protein involved in one or both of blood coagulation and fibrinolysis.

In an alternative embodiment the protein formulation comprises an antibiotic.

Operation of the delivery device will now be described hereinbelow with reference to FIG. 3 of the accompanying drawings.

The nosepiece 17 is first inserted into one of the nasal cavities of a subject until the nosepiece 20 abuts the nares of the nostril, at which point the distal end of the outlet unit 21 extends about 2 cm into the nasal cavity of the subject, and the mouthpiece 19 is gripped in the lips of the subject.

The subject then begins to exhale through the mouthpiece 19, which exhalation acts to close the oropharyngeal velum of the subject and drive an air flow through the delivery channel 23 of the outlet unit 21, with the air flow passing into the one nasal cavity, around the posterior margin of the nasal septum and out of the other nasal cavity, thereby achieving a bi-directional air flow through the nasal airway of the subject.

In this embodiment, when the flow rate developed through the delivery channel 23 reaches a predetermined value, the release mechanism 31 is triggered to actuate the substance supply unit 29 to deliver a metered dose of the nasal formulation to the nozzle 25 and into the nasal cavity of the subject as an aerosol spray.

In this embodiment, where the delivery device is a multi-dose device, the device is ready for further use following priming of the substance supply unit 29.

Finally, it will be understood that the present invention has been described in its preferred embodiments and can be modified in many different ways without departing from the scope of the invention as defined by the appended claims.

Figure 4:
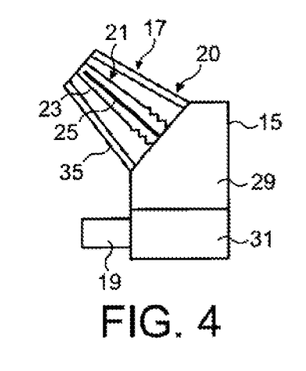
FIG. 4 illustrates a nasal delivery device as one modification of the first-described embodiment, with an outer sleeve of the nosepiece fitted.
Figure 5:
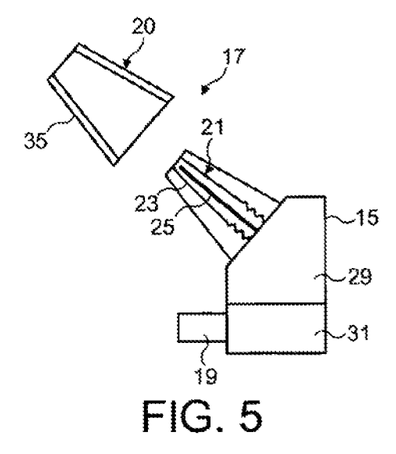
FIG. 5 illustrates the delivery device of FIG. 4, with the outer sleeve of the nosepiece removed.

In one modification of the above-described device, as illustrated in FIGS. 4 and 5, the nosepiece 20 could include a replaceable outer sleeve 35, which allows for replacement at periodic intervals, for example, after each operation. FIGS. 4 and 5 illustrate the sleeve 35 when fitted and removed, respectively.

Figure 6:
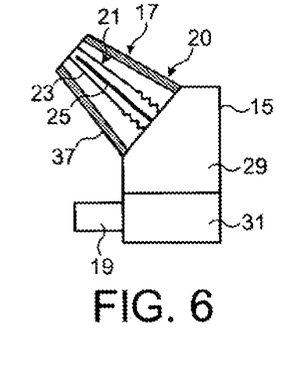
FIG. 6 illustrates a nasal delivery device as another modification of the first-described embodiment.
Figure 7:
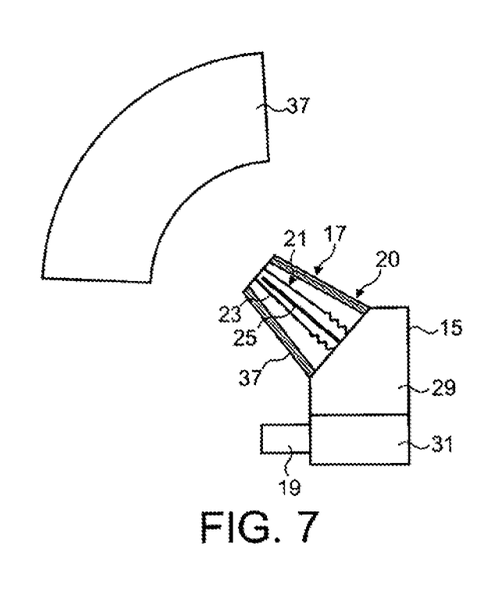
FIG. 7 illustrates the delivery device of FIG. 6, with a sleeve of the nosepiece removed.

In one embodiment the sleeve 35 can include an indicator material which provides an indication of exposure to one or more of moisture and biomaterials, for example, endotoxins, thereby providing an indication to the user when the sleeve 35 should be replaced.

In another modification of the above-described device, as illustrated in FIGS. 6 and 7, the nosepiece 20 could include a plurality of removable sleeves 37, typically formed as thin films, which are peelable successively to allow for exposure of a fresh sleeve 37 at periodic intervals, for example, after each operation.

In one embodiment one or more of the innermost sleeves 37 can be marked, for example, colored, to indicate that a minimum number of the sleeves 37 remain.

In one embodiment the sleeves 37 can include an indicator material which provides an indication of exposure to one or more of moisture and biomaterials, for example, endotoxins, thereby providing an indication to the user when the outer sleeve 37 should be discarded.

Furthermore, in the above-described embodiment the delivery device is configured to deliver an air flow through one nostril of a subject at such a pressure as to flow around the posterior margin of the nasal septum and out of the other nostril of the subject, thereby achieving bi-directional delivery through the nasal cavities as disclosed in WO-A-2000/51672, the content of which is herein incorporated by reference, but in an alternative embodiment the delivery device could be configured to deliver an air flow which is not sufficient to achieve bi-directional delivery through the nasal cavities or utilizes no entraining gas flow. This embodiment is still advantageous as compared to known delivery devices, in providing for velum closure and being capable of achieving targeted delivery, particularly when certain regions of the nasal cavity are obstructed by cuff members.

In another alternative embodiment the above-described delivery device could be configured not to provide for any gas flow, but instead provide for targeted delivery through use of an optimized nosepiece.

REFERENCES

1. Baker, L D et al, Acute intranasal insulin administration improves verbal memory for adults with Alzheimer's disease, Society for Neuroscience Abstract Viewer and Itinerary Planner 2003, Abstract No 84.17.
2. Benedict, C et al, Intranasal insulin improves memory in humans, Psychoneuroendocrinology, November 2004, 29, pages 1326-34.
3. Born, J et al, Sniffing neuropeptides: a transnasal approach to the human brain, Nat Neurosci, June 2002, 5(6), pages 514-6.
4. Fehm, L et al, Body weight regulation through the central nervous system. The development of a pathogenetically based adiposity therapy, Med Klin (Munich), November 2004, 99(11), pages 674-9.
5. Hallschmid, M et al, Intranasal insulin reduces body fat in men but not in women, Diabetes, November 2004, 53, pages 3024-9.
6. Hallschmid, M et al, Manipulating central nervous mechanisms of food intake and body weight regulation by intranasal administration of neuropeptides in man, Physiol Behav, October 2004, 83, pages 55-64.
7. Stockhorst, U et al, Insulin and the CNS: effects on food intake, memory, and endocrine parameters and the role of intranasal insulin administration in humans, Physiol Behav, October 2004, 83, pages 47-54.
8. Watson, G S et al, Insulin effects on CSF norepinephrine and cognition in Alzheimer's disease, Neurobiology of Aging, Jan. 2006, 27(1), pages 38 to 41.
9. Harrison, L C et al, Administration of Intranasal Insulin to Humans At Risk for Type I Diabetes, Diabetes Care, 2004, 27 pages 2348-2355.
10. Cole, P, The Respiratory Role of the Upper Airways, a selective clinical and pathophysiological review. 1993, Mosby-Year Book Inc. ISBN1.55664-390-X.
11. Rosenberger, H, Growth and Development of the Naso-Respiratory Area in Childhood, PhD Thesis, Laboratory of Anatomy, School of Medicine, Western Reserve University, Presented to the Annual Meeting of the American Laryngological, Rhinological and Otological Society, Charleston, S.C., USA, 1934.
12. Zacharek, M A et al, Sagittal and Coronal Dimensions of the Ethmoid Roof: A Radioanatomic Study, Am J Rhinol 2005, 19, pages 348-352.
13. Bakke H et al, Oral Spray Immunization May Be an Alternative to Intranasal Vaccine Delivery to Induce Systemic Antibodies but not Nasal Mucosal or Cellular Immunity, Scandinavian Journal of Immunology, March 2006, 63, pages 223-31.
14. Brandtzeg P et al, Role of secretory antibodies in the defence against infections, Int J Med Microbiol, April 2003, 293(1), pages 3-15. For the avoidance of doubt, the contents of the above-identified references are herein incorporated by reference.

What is claimed is:

1. A method of delivering a protein formulation to the upper posterior region of a nasal cavity of a subject for uptake into the central nervous system (CNS) of the subject, the method comprising the steps of:
    delivering the formulation through a nozzle of a nosepiece of a delivery device into the nasal cavity of the subject to provide for uptake of the protein to the CNS without triggering an immune response; and
    the subject exhaling through a mouthpiece unit to cause closure of the oropharyngeal velum of the subject;
    wherein air exhaled from an exhalation breath is delivered through the nosepiece to entrain the protein formulation as delivered from the nozzle; and
    wherein the nosepiece includes a coating which prevents the accumulation of endotoxins thereon.
2. The method of claim 1, wherein the protein comprises a corticotrophic releasing hormone.
3. The method of claim 2, wherein the corticotrophic releasing hormone is corticorelin.
4. The method of claim 1, wherein the protein comprises a somatotrophic hormone receptor antagonist.
5. The method of claim 4, wherein the somatotrophic hormone receptor antagonist is pegvisomant.
6. The method of claim 1, wherein the protein comprises insulin or an insulin analogue.
7. The method of claim 1, wherein the coating degrades endotoxin polysaccharides.
8. The method of claim 1, wherein the nosepiece is replaceable.
9. The method of claim 1, wherein the delivery device further comprises an outer sleeve that covers the nosepiece.
10. The method of claim 9, wherein the outer sleeve includes an indicator material which indicates exposure to one or more of moisture and biomaterials.
11. The method of claim 10, wherein the indicator material of the outer sleeve indicates exposure to endotoxins.
12. The method of claim 1, wherein the delivery device further comprises a plurality of removable outer sleeves, each of the plurality of outer sleeves configured to cover the nosepiece.
13. The method of claim 12, wherein each of the plurality of removable outer sleeves includes an indicator material which indicates exposure to one or more of moisture and biomaterials.

14. The method of claim 1, wherein the nosepiece includes an anti-bacterial coating which degrades endotoxin polysaccharides.

15. A method of delivering a protein formulation to the upper posterior region of a nasal cavity of a subject for uptake into the CNS of the subject, the method comprising the steps of:
delivering the formulation through a nozzle of a nosepiece of a delivery device into the nasal cavity of the subject to provide for uptake of the protein to the CNS without triggering an immune response; and
delivering a gas flow, separate to an exhaled air flow from an exhalation breath of the subject, to the nosepiece to entrain the protein formulation as delivered from the nozzle; and
wherein the nosepiece includes a coating which prevents the accumulation of endotoxins thereon.

16. The method of claim 15, wherein the protein comprises insulin or an insulin analogue.

17. The method of claim 15, wherein the coating degrades endotoxin polysaccharides.

18. The method of claim 15, wherein the nosepiece is replaceable.

19. The method of claim 15, wherein the delivery device further comprises an outer sleeve that covers the nosepiece.

20. The method of claim 13, wherein the outer sleeve includes an indicator material which indicates exposure to one or more of moisture and biomaterials.

21. The method of claim 20, wherein the indicator material of the outer sleeve indicates exposure to endotoxins.

22. The method of claim 15, wherein the delivery device further comprises a plurality of removable outer sleeves, each of the plurality of outer sleeves configured to cover the nosepiece.

23. The method of claim 16, wherein each of the plurality of removable outer sleeves includes an indicator material which indicates exposure to one or more of moisture and biomaterials.

24. The method of claim 15, wherein the nosepiece includes an anti-bacterial coating which degrades endotoxin polysaccharides.

25. A method of delivering insulin or an insulin analogue to a subject, the method comprising:
delivering a therapeutically effective amount of a formulation consisting essentially of insulin or an insulin analogue in solubilized or power form through a nozzle of a nosepiece of a delivery device to the olfactory bulb in the upper posterior region of a nasal cavity of the subject for uptake of the insulin or insulin analogue into the central nervous system of the subject without triggering an immune response; and
causing the subject to exhale through a mouthpiece unit of the delivery device to cause closure of the oropharyngeal velum of the subject; wherein air exhaled from an exhalation breath of the subject is delivered through the nosepiece to entrain the formulation as delivered from the nozzle; and
wherein the nosepiece includes a coating which prevents the accumulation of endotoxins thereon.

26. The method of claim 25, wherein the delivery of the formulation is under conditions that avoid presentation to nasal associated lymphatic tissue (NALT), adenoids, antigen presenting cells (APCs), and nasal mucosa.

27. The method of claim 25, wherein the coating degrades endotoxin polysaccharides.

28. The method of claim 25, wherein the nosepiece is replaceable.

29. The method of claim 25, wherein the delivery device further comprises an outer sleeve that covers the nosepiece.

30. The method of claim 29, wherein the outer sleeve includes an indicator material which indicates exposure to one or more of moisture and biomaterials.

31. The method of claim 30, wherein the indicator material of the outer sleeve indicates exposure to endotoxins.

32. The method of claim 25, wherein the delivery device further comprises a plurality of removable outer sleeves, each of the plurality of outer sleeves configured to cover the nosepiece.

33. The method of claim 32, wherein each of the plurality of removable outer sleeves includes an indicator material which indicates exposure to one or more of moisture and biomaterials.

34. The method of claim 25, wherein the nosepiece includes an anti-bacterial coating which degrades endotoxin polysaccharides.

* * * * *